United States Patent [19]

Kempf

[11] Patent Number: 4,585,446

[45] Date of Patent: Apr. 29, 1986

[54] DIALYSIS NEEDLE

[76] Inventor: Joseph Kempf, 121 S. Vernon St., Princeton, Ill. 61356

[21] Appl. No.: 590,497

[22] Filed: Mar. 16, 1984

[51] Int. Cl.$^4$ ............................................. A61M 5/005
[52] U.S. Cl. .................................. 604/274; 604/117; 604/411
[58] Field of Search ............... 604/274, 272, 271, 264, 604/117, 411, 414

[56] References Cited

U.S. PATENT DOCUMENTS

| | | | |
|---|---|---|---|
| 1,150,387 | 8/1915 | Roberts | 604/274 |
| 2,601,580 | 6/1952 | Yanus | 604/274 |
| 2,862,495 | 12/1958 | Gewecke | 604/274 |
| 2,989,053 | 6/1961 | Hamilton | 604/274 |
| 3,119,391 | 1/1964 | Harrison | 604/274 |
| 3,633,580 | 1/1972 | Knox | 604/274 |
| 3,645,268 | 2/1972 | Capote | 604/274 |
| 3,831,814 | 8/1974 | Butler | 604/274 |
| 3,906,932 | 9/1975 | Ayres | 604/274 |

Primary Examiner—C. Fred Rosenbaum
Assistant Examiner—Gene B. Kartchner
Attorney, Agent, or Firm—McCaleb, Lucas & Brugman

[57] ABSTRACT

A dialysis needle or the like comprises a tube with a razor edged cutting blade extending diametrically across its forward end. The blade has a generally "V" shape with a pair of razor sharp cutting edges converging forwardly from opposite sides of the tube and terminating in a needle-sharp point. A pair of diametrically opposed, smooth, tissue-spreading ribs are located in a plane normal to the cutting edges and converge forwardly from opposite sides of the tube to positions immediately rearwardly adjacent of the point. Two specific embodiments are described: an all-stainless-steel version; and a plastic version with a cutting blade insert.

10 Claims, 9 Drawing Figures

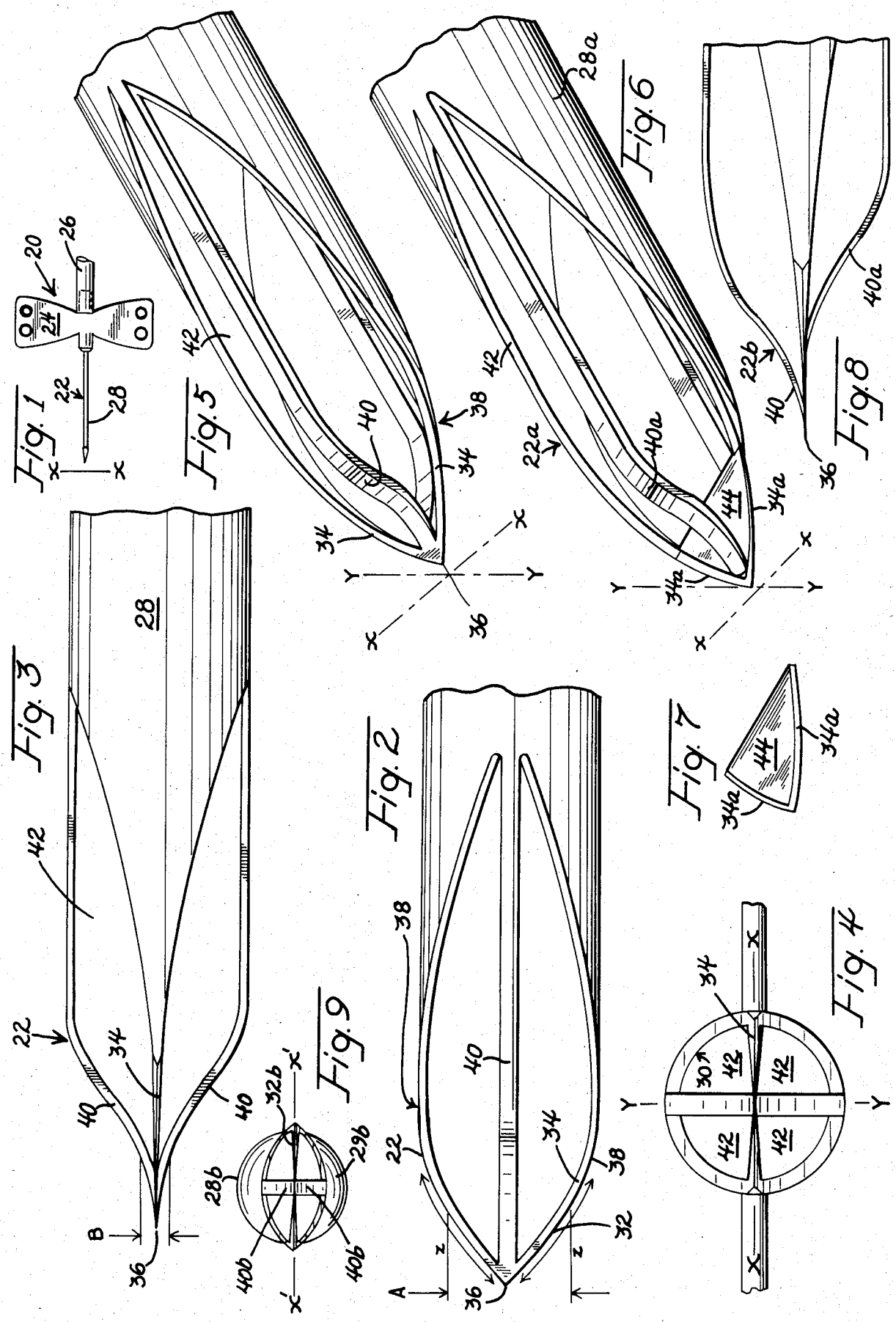

DIALYSIS NEEDLE

BACKGROUND OF THE INVENTION

This invention relates generally to medical procedures such as hemodialysis in which blood is drawn from a blood vessel for treatment by an artificial kidney machine, and returned to a patient whose kidneys are unable to properly cleanse the blood. In dialysis, as this procedure is called, two needles are inserted in separate blood vessels, and connected by sterile rubber-like or plastic tubing to inlet and outlet ports of an artificial kidney machine.

Because of the large volume of blood that must be handled, and the several hours time required for each treatment, the needles are very large. Typically, they are made of steel tubing up to 15-gauge in size (approximately 1/12th inch diameter) sharpened by making a double bevel cut across their forward end.

A kidney dialysis patient must undergo this treatment as often as three times a week, sometimes every other day, and as much as four hours each time. The repeated penetration of the blood vessels by these large relatively dull needles is exceedingly painful and causes severe trauma to the blood vessels and overlying tissues. Favored locations for the needles are in the forearm where they are inserted into four- to six-inch segments of the blood vessels themselves, or in substitute sections called "Gortex" or "Bovine" grafts.

Various locations in the forearm, the upperarm and the legs are used as access points for dialysis needles. Healing is often slow because the blood chemistry of dialysis patients is not ideal for rapid healing. If the patient's blood vessels fail to regenerate themselves, or scar tissue from repeated needle insertions prevents adequate blood flow, the blood vessels are in effect worn out, the patient has no more access points, and he or she dies.

There are several problems inherent in these conventional large diameter, bevel cut dialysis needles.

In the first place, these large 15-gauge needles simply cannot be sharpened effectively by the bevel-cut method. This method works well on small hypodermic needles of 27-gauge (1/60th inch diameter) or smaller. However, the bevel-sharpening technique does not operate effectively on large diameter dialysis needles; this technique does not make them sharp enough to avoid painful penetration, and trauma to the tissues and blood vessels.

Another problem arises out of the necessity to thread the dialysis needle a full inch or more into the blood vessel to stabilize it for the hours-long procedure. This is difficult to do because the large-diameter needle is roughly the size of the inside diameter of the blood vessel, and the sharpened tip, which is offcenter of the conventional needle, tends to get caught in the blood vessel wall and go right on through the other side. This is a serious, common mishap called "infiltration".

Another problem with the conventional needles is that after they are in place and the dialysis machine in operation, the fluid volume of blood in the patient decreases. The blood pressure then falls and the vein containing the withdrawal needle may collapse across the beveled opening at the front of the needle, acting like a check or flap valve and shutting off flow. When this happens, the machine goes into an alarm condition and the operator or attendant has to take emergency countermeasures to re-start normal flow.

Despite the before-mentioned drawbacks, the only dialysis needles in common use are the bevel-cut tubes described.

SUMMARY OF THE INVENTION

It is a general object of this invention to provide a dialysis needle or the like with improved patient comfort and minimal trauma in the blood vessels.

Another object of the invention is to provide such a dialysis needle with a razor-edged cutting blade which can be effectively used with large diameter needles.

Another object is to provide such a needle which can be threaded deeply into a blood vessel without infiltrating it.

Another object is to provide such a needle which will not shut off involuntarily when the patient's blood pressure drops.

Another object is to provide a needle comprising a "V" shaped, razor edged cutter blade converging forwardly from opposite sides of a tube to a needle sharp point, and a pair of diametrically-opposed, tissue-spreading ribs located between the cutting blades and converging forwardly from opposite sides of the tube to positions spaced rearwardly of the point.

Another object is to provide such a needle with blood flow openings between the cutter blade and the tissue-spreading ribs, arranged so it is impossible for all of the openings to be closed off simultaneously by collapse of the blood vessel wall as these openings are held open by the ribs.

Another object is to provide such a needle in which the cutting blade and the tissue-spreading ribs are in separate, longitudinal planes at substantially right angles to one another and extending along the axis of the tube.

Another object is to provide such a needle in which the tissue-spreading ribs are disposed at different distances behind the point.

Another object is to provide such a needle having a planar guide member parallel to the cutting blade to serve as a guide for inserting the needle and holding it in the blood vessel.

BRIEF DESCRIPTION OF THE DRAWING

Other objects and advantages will be apparent from the following description taken in connection with the accompanying drawing which:

FIG. 1 is a top plan view of a dialysis needle assembly illustrating a preferred form of the present invention.

FIG. 2 is a fragmentary enlarged view of the forward portion of the improved needle shown in FIG. 1.

FIG. 3 is a side view of FIG. 2.

FIG. 4 is a front end view of FIGS. 2 and 3.

FIG. 5 is a perspective view of the needle portion shown in FIGS. 2 and 3.

FIG. 6 is a perspective view, similar to FIG. 5, of an alternate embodiment employing a cutter blade insert.

FIG. 7 is a perspective view of the cutter blade insert shown in FIG. 6.

FIG. 8 is a view similar to FIG. 3 of a further alternate embodiment of the invention.

FIG. 9 is a view similar to FIG. 4 of a still further embodiment of the invention.

Like parts are referred to by like reference characters throughout the figures of the drawing.

DESCRIPTION OF THE PREFERRED EMBODIMENTS

Referring now to the specific embodiments of the invention in the drawings, the dialysis needle assembly shown in FIG. 1 is generally designated 20. It comprises a needle 22 and a flat tab or "butterfly" guiding element 24. In use, it is attached to a flexible rubberlike or plastic tubing 26 which is connected to a kidney dialysis machine (not shown).

Referring first to the improved dialysis needle 22 shown in FIGS. 1-5, it comprises a cylindrical tube 28 of stainless steel having any suitable length and an outside diameter of 15-gauge (0.072 inches) in a typical example. The tube has an internal bore 30 through which blood (or fluid, if the needle is used for intravenous feeding for example) flows. The embodiment shown in FIGS. 1-5 is all metal, for example, stainless steel.

At the front end (to the left in the drawing), the tube 28 is formed with a "V" shaped cutter blade 32 having a pair of razor sharp cutting edges 34,34 converging forwardly to a centrally located needle sharp point 36.

An important part of the invention is that the razor sharp cutting edges 34,34 extend outwardly from the point 36 only so far as indicated by the arrows in FIG. 2. Thus, they are no wider than the diameter of the tube 28 to avoid cutting the inside wall of the blood vessel when the needle is fully inserted into operating position and centered within the vessel. Preferably, the outer limits 38 of the cutting edges 34 should be within the outside diameter of the tube as best shown in FIG. 2.

A pair of diametrically opposed, smooth, tissue-spreading ribs 40 are located at the front of the tube midway between the cutting edges 34,34 and converge forwardly from opposite sides of the tube to positions spaced rearwardly of the point 36. For maximum patient comfort and to facilitate painless insertion of the needle, it is also important that the tissue be incised by the cutting edges 34 before the incision is spread open by the ribs 40. To this end, the transverse width of the cutter blade 32 progressively increases from front to back at a greater rate than the spacing between the outside surfaces of the ribs 40. This is best illustrated by comparing FIGS. 2 and 3 where the width of cutting blade 32 at one point is shown as a relatively wide dimension A substantially greater than the spacing B beteen ribs 40 at the same insertion depth. One way of achieving this relationship in the critical forward position of the needle is to provide the ribs 40 with significantly concave outer contours, as shown in FIGS. 2 and 3 respectively.

FIG. 3 shows the tissue-spreading ribs 40 in a symmetrical relationship in which the forward ends of both terminate at some distance behind the point 36. FIG. 8 shows an alternate, unsymmetrical relationship in which the forward end of rib 40a terminates at a greater distance behind the point 36 than the forward end of rib 40.

As best shown in the end view of FIG. 4, four blood flow openings 42 are provided between cutting edges 34 and ribs 40. Further, these openings extend a substantial distance backwardly along the needle. This wide dispersal of openings, their elongated contours, and the diametrically opposed ribs 40, all combine to hold a blood vessel positively open and prevent shut-off flow due to collapse onto the withdrawal needle as can occur with a conventional bevel cut needle.

While the embodiment of FIGS. 1-5 is made of a single material such as stainless steel, an alternative construction shown in FIGS. 6 and 7 has a tube 28a and ribs 40a made of plastic material such as nylon with a forward, generally triangle-shaped cutting blade insert 44 of stainless steel or other suitable metal having forwardly converging, ogive cutting edges 34a,34a.

When inserting, it is important to orient the needle so the plane X—X (FIGS. 1, 4, 5 and 6) of the cutting blade 32 or 44 is at an acute angle typically about 45 degrees relative to the plane of the patient's skin. As a guide to maintain this orientation, the flat, plastic tab or "butterfly" 24 is provided at the rear end of the needle. After the razor-sharp edge parts the skin and then the vein or artery wall at this 45 degree angle, one of the smooth ribs 40 will bottom out against the far side of the vein wall. The needle can then be inclined more nearly parallel to the vein and pushed or threaded farther into it. After insertion to about one inch or more in the blood vessel, the butterfly can be taped to the skin and the smooth ribs 40 and outside wall of the tube 28 will maintain the needle centered in the vessel with no possibility of the point 36 or either of the cutting edges 34,34 (or 34a,34a) engaging and cutting the inner wall of the vessel.

The needle of the present invention has been described by way of illustration, and not by way of limitation, for use in dialysis procedures. Other uses outside of dialysis include blood donations and transfusions where the improved needle would be more comfortable, less painful, and generally more effective than conventional needles. Furthermore, while its advantages have been described for large diameter needles, many of the same benefits would apply for small diameter needles.

The invention is not necessarily limited to perfectly round tubular cross-sections. For example, FIG. 9 illustrates a still further embodiment in which a round cross-section tube 28b has a forwardly projecting tubular section 29b of oval cross-section with a cutter blade 32a extending fully across its width along the long axis X'—X' of the oval. Ribs 40b are counterparts of the previously-described ribs 40 and 40a. The FIG. 9 embodiment enables the length of the incision made by the cutter blade 32a to be closer to the circumference of the tube 28b. This minimizes stretching and tearing of the incision to permit entry of the tube 28b with minimal trauma of the blood vessel; and facilitates rapid healing.

The embodiments described and shown to illustrate the present invention have been necessarily specific for purposes of illustration. Alterations, extensions and modifications would be apparent to those skilled in the art. As one example, the point 36 may be positioned slightly offcenter in the embodiments shown. The aim of the appended claims, therefore, is to cover all variations included within the spirit and scope of the invention.

The embodiments of the invention in which an exclusive property or privilege is claimed are defined as follows:

1. A dialysis needle or the like comprising:
   a tube with a wall having a bore extending therethrough;
   a razor-edged cutting blade extending transversely across the forward end of said tube, said blade having a generally "V" shape with a pair of razor-sharp cutting edges diverging rearwardly from a centrally-located needle-sharp point to opposite sides of the tube;

a pair of transversely-opposed smooth, tissue-spreading ribs located between the cutting edges and diverging rearwardly from said point to opposite sides of the tube;

forwardly open openings between the cutting edges and tissue-spreading ribs providing fluid flow passages extending rearwardly from the point to the rear ends of the ribs and communicating with said bore and the transverse widths across the cutting edges and across the ribs progressively increasing from the point rearwardly at different rates to enable coincidental incising and spreading of tissue without pulling the ends of the incision apart and taut against the cutting edges.

2. A dialysis needle or the like according to claim 1 in which the cutting blade extends diametrically across the forward end of the tube in a first plane parallel to the centerline of the tube, and the tissue-spreading ribs are in a second plane normal thereto.

3. A dialysis needle or the like according to claim 2 in which the transverse width of the cutting blade progressively increases from front to back at a greater rate than the transverse spacing between the tissue-spreading ribs to insure that tissue is incised before the incision is spread by the ribs.

4. A dialysis needle or the like according to claim 3 in which the tissue-spreading ribs are formed with significantly concave outer contours and the cutting edges are formed with significantly convex outer contours.

5. A dialysis needle or the like according to claim 1 in which said razor-edged cutting blade has a width approximating the outside diameter of the tube whereby said ribs and tube wall will maintain the needle centered in a blood vessel with no possibility of said point or cutting blade engaging and cutting the inner wall of the vessel.

6. A dialysis needle or the like according to claim 1 in which said razor-edged cutting blade has a width less than the outside diameter of the tube whereby said ribs and tube wall will maintain the needle centered in a blood vessel with no possibility of said point or cutting blade engaging and cutting the inner wall of the vessel.

7. A dialysis needle or the like according to claim 1 in which said tube is made of non-metallic material and said razor-edged cutting blade is of metal implanted into the leading edge of said wall.

8. A dialysis needle or the like according to claim 7 in which said tube is made of plastic material.

9. A dialysis needle or the like according to claim 1 having a planar guide member connected to the rear end thereof, said planar guide member comprising a pair of flat tabs extending on opposite sides of the needle and being coplanar with said cutting blade and effective for use as a guide and holder to maintain said cutting blade parallel to the surface of a patient's skin during and after emplacement of the needle in a blood vessel.

10. A dialysis needle or the like according to claim 1 in which the rear end portion of the tube has a round cross-section and at least the forward end of said tube is oval in cross-section and the cutting blade extends along the long axis of the oval cross-section the full length thereof.

* * * * *